(12) United States Patent
Gers-Barlag et al.

(10) Patent No.: US 6,368,578 B1
(45) Date of Patent: Apr. 9, 2002

(54) COSMETIC AND DERMATOLOGICAL LIGHT PROTECTION FORMULATIONS WITH A CONTENT OF ASYMMETRICALLY SUBSTITUTED TRIAZINE DERIVATIVES AND ALKYL NAPHTHALATES

(75) Inventors: Heinrich Gers-Barlag, Kummerfeld; Volker Wendel, Hamburg; Wiebke Grundt, Buchholz, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/793,192

(22) Filed: Feb. 26, 2001

(30) Foreign Application Priority Data

Feb. 25, 2000 (DE) .......................... 100 08 894

(51) Int. Cl.[7] .............. A61K 7/42; A61K 7/44; A61K 7/00; A61K 31/53
(52) U.S. Cl. ............ 424/59; 424/60; 424/400; 424/401; 514/241
(58) Field of Search .................. 424/59, 60, 400, 424/401; 514/241

(56) References Cited

U.S. PATENT DOCUMENTS 5,738,842 A * 4/1998 Raspanti et al. ............. 424/59
5,759,525 A * 6/1998 Raspanti et al. ............. 424/59
5,993,789 A * 11/1999 Bonda et al. ................. 424/59

\* cited by examiner

*Primary Examiner*—Shelley A. Dodson
(74) *Attorney, Agent, or Firm*—Norris McLaughlin & Marcus

(57) ABSTRACT

An active ingredient combination effective for light protection and composed of (a) one or more UV filter substances selected from the group of asymmetrically substituted triazine derivatives and (b) one or more dialkyl naphthalates having the structural formula

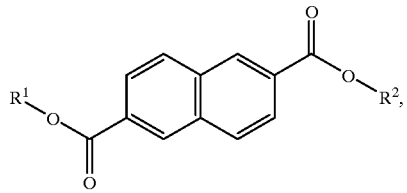

in which $R^1$ and $R^2$ are, independently of one another, selected from the group of branched and unbranched alkyl groups having 6 to 24 carbon atoms.

6 Claims, No Drawings

COSMETIC AND DERMATOLOGICAL LIGHT PROTECTION FORMULATIONS WITH A CONTENT OF ASYMMETRICALLY SUBSTITUTED TRIAZINE DERIVATIVES AND ALKYL NAPHTHALATES

The present invention relates to cosmetic and dermatological light protection preparations, in particular skin-care cosmetic and dermatological light protection preparations.

The harmful effect of the ultraviolet part of solar radiation on the skin is generally known. The rays have various effects on the skin as an organ depending on their particular wavelength; so-called UV-C radiation with a wavelength below 290 nm is absorbed by the ozone layer in the earth's atmosphere and therefore has no physiological significance. By contrast, rays in the range between 290 nm and 320 nm, the so-called UV-B range, cause erythema, simple sunburn or even more or less severe burns. The narrower range around 308 nm is stated to be a maximum for the erythema activity of sunlight.

Numerous compounds are known for protecting against UV-B radiation, examples thereof being derivatives of 3-benzylidenecamphor, of 4-aminobenzoic acid, of cinnamic acid, of salicylic acid, of benzophenone, of 2-phenylbenzimidazole and of s-triazine.

It has long been incorrectly assumed that the long-wavelength UV-A radiation with a wavelength between 320 nm and 400 nm has only a negligible biological effect. However, it has now been proved by many studies that UV-A radiation is far more hazardous than UV-B radiation in relation to the initiation of photodynamic, specifically phototoxic, reactions and chronic changes in the skin.

Thus, it has been proved, inter alia, that even UV-A radiation under entirely normal everyday conditions is sufficient to damage within a short time the collagen and elastin fibers which are of essential importance for the structure and firmness of the skin. This results in chronic light-induced skin changes—the skin "ages" prematurely. The clinical appearance of skin aged by light includes, for example, creases and wrinkles and an irregular, furrowed relief. In addition, the areas affected by light-induced skin aging may have irregular pigmentation. The formation of brown spots, keratoses and even carcinomas or malignant melanomas is also possible. Skin aged prematurely by everyday exposure to UV is additionally distinguished by a lower activity of the Langerhans cells and a slight chronic inflammation.

About 90% of the ultraviolet radiation which reaches the earth consists of UV-A rays. Whereas UV-B radiation varies greatly depending on a large number of factors (for example season and time of day or latitude), UV-A radiation remains relatively constant from day to day irrespective of seasonal and diurnal or geographic factors. At the same time, most of the UV-A radiation penetrates into living epidermis, while about 70% of UV-B rays are retained by the stratum corneum.

It is therefore of fundamental importance that cosmetic and dermatological light protection preparations provide adequate protection both against UV-B and against UV-A radiation.

In general, the light absorption characteristics of light protection filter substances are very well known and documented, especially since most industrialized countries have positive lists for the use of such substances, which impose very strict standards on the documentation.

The use concentration of known light protection filter substances is, however, frequently limited in particular in combination with other substances present as solids. There are thus certain technical difficulties in formulating to achieve higher sun protection factors and effective UV-A protection.

Various authors have introduced UV filter substances having the structural motif

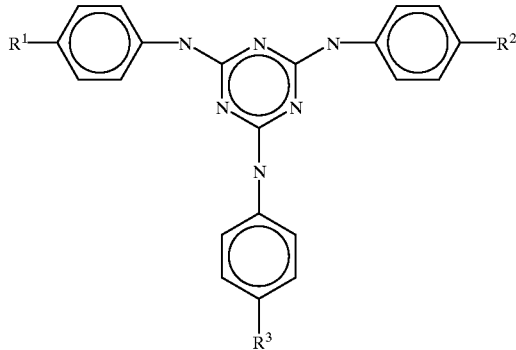

Both symmetrical substitution and asymmetrical substitution in relation to the $C_3$ axis of the triazine basic structure are conceivable. In this sense, symmetrically substituted s-triazines have three identical subsituents $R^1$, $R^2$ and $R^3$, while asymmetrically substituted s-triazine accordingly have different substituents, thus destroying the $C_3$ symmetry. For the purpose of the present invention, "asymmetric" always means asymmetric in relation to the $C_3$ axis of the triazine basic structure, unless anything else is expressly mentioned.

Asymmetrically substituted triazine derivatives display a good light protection effect. Their main disadvantage is, however, that their solubility is low in conventional oil components. Well-known solvents can dissolve only up to a maximum of 15% by weight of these compounds, which usually corresponds to a concentration of about 1 to 1.5% by weight of dissolved (=active) filter substance in the complete cosmetic or dermatological preparation.

One disadvantage of the prior art is accordingly that generally only comparatively low sun protection factors have been achievable with these filter substances because their solubility or dispersibility in the formulations is too low, i.e. they can be satisfactorily incorporated into such formulations only with difficulty or not at all.

Even if it is also possible in principle to achieve a certain UV protection when the solublity is limited, another problem frequently occurs, that is recrystallization. Substances of low solubility in particular recrystallize comparatively rapidly, which may be induced by fluctuations in temperature or other influences. Uncontrolled recrystallization of an essential ingredient of a preparation such as a UV filter has, however, extremely disadvantageous effects on the properties of the given preparation and, not least, on the desired light protection.

It was an object of the present invention to obtain in a simple manner preparations which are distinguished by an increased content of asymmetrically substituted triazine derivatives and a correspondingly high sun protection factor.

It was, however, surprising and not predictable for the skilled worker that the disadvantages of the prior art are remedied by active ingredient combinations effective for light protection and composed of
  (a) one or more UV filter substances selected from the group of asymmetrically substituted triazine derivatives and
  (b) one or more dialkyl naphthalates having the structural formula

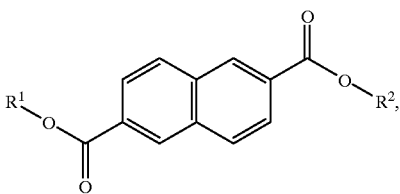

in which $R^1$ and $R^2$ are, independently of one another, selected from the group of branched and unbranched alkyl groups having 6 to 24 carbon atoms.

Also according to the invention is, in particular, the use of one or more dialkyl naphthalates having the structural formula

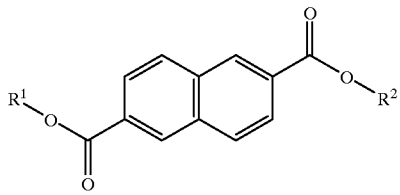

in which $R^1$ and $R^2$ are, independently of one another, selected from the group of branched and unbranched alkyl groups having 6 to 24 carbon atoms, as solvent, solution aid, solubilizer or stabilizer for asymmetrically substituted triazine derivatives.

In a particularly advantageous embodiment, the present invention relates to the use of one or more dialkyl naphthalates having the structural formula

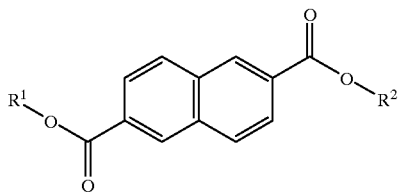

in which $R^1$ and $R^2$ are, independently of one another, selected from the group of branched and unbranched alkyl groups having 6 to 24 carbon atoms, for achieving or increasing the solubility of asymmetrically substituted triazine derivatives in (a) either an isolated oil component or (b) at least one oil phase of a disperse two-phase or multiphase system which may additionally comprise one or more aqueous phases.

It is preferred according to the invention for the disperse two-phase or multiphase systems which, besides one or more oil phases, may additionally comprise one or more aqueous phases to be constituted in the form of cosmetic or dermatological emulsions—for example of the W/O, O/W, W/O/W or O/W/O type. Such emulsions may preferably also be a microemulsion, a Pickering emulsion or a sprayable emulsion. It may, however, also be advantageous for the preparations of the invention to be a solution, a hydrodispersion, an aerosol, a foam or else a stick.

Dialkyl naphthalates advantageous for the purpose of the present invention are those where $R^1$ and/or $R^2$ are branched alkyl groups having 6 to 10 carbon atoms. Diethylhexyl naphthalate is very particularly preferred.

Advantageous asymmetrically substituted s-triazine derivatives within the meaning of the present invention are, for example, those described in EP-A-570 838, whose chemical structure is represented by the generic formula

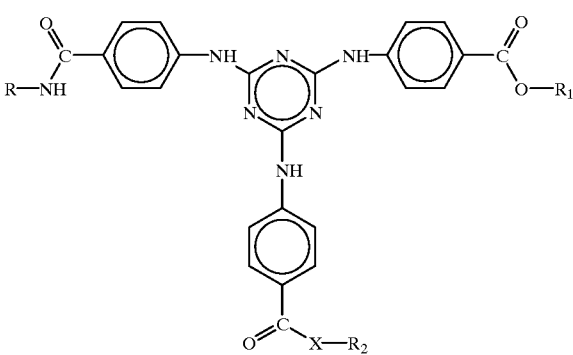

where

R is a branched or unbranched $C_1$–$C_{18}$-alkyl radical, a $C_5$–$C_{12}$-cycloalkyl radical, optionally substituted by one or more $C_1$–$C_4$-alkyl groups, and X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

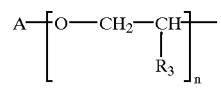

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted by one or more $C_1$–$C_4$-alkyl groups, and if X is the NH group, a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

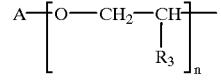

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, if X is an oxygen atom.

In a preferred embodiment, the present invention relates to cosmetic or dermatological formulations with a content of least one asymmetrically substituted s-triazine selected from the group of substances described in EP-A-775 698:

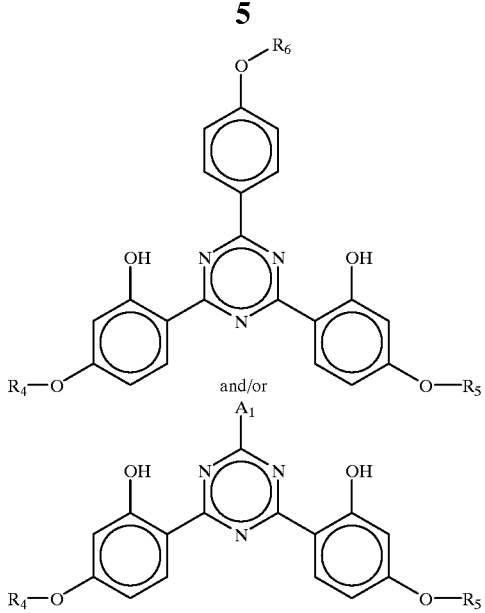

All the bisresorcinyltriazines mentioned in this publication whether disclosed by generic or by specific formulae, are advantageous for the purpose of the present invention. $R_4$ and $R_5$ are very particularly advantageously selected from the group of branched or unbranched alkyl groups of 1 to 18 carbon atoms. The alkyl groups may also again advantageously be substituted by silyloxy groups.

$A_1$ is advantageously a substituted homocyclic or heterocyclic aromatic five-membered ring or six-membered ring.

The following compounds are very particularly advantageous:

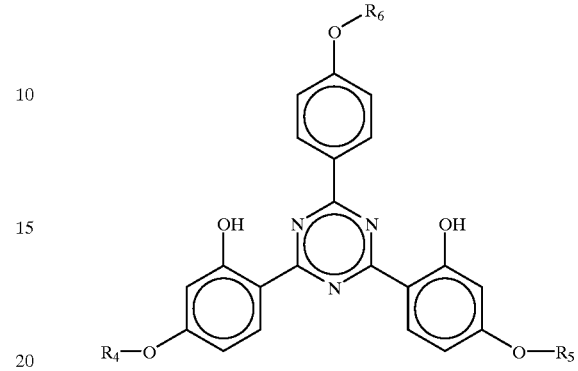

where $R_6$ is a hydrogen atom or a branched or unbranched alkyl group with 1 to 10 carbon atoms, in particular 2,4-bis{[4-(2-ethylhexyloxy)-2-hydroxy]phenyl}-6-(4-methoxyphenyl)-1,3,5-triazine (INCI: aniso triazine), which is obtainable under the proprietary name Tinosorb® S from CIBA-Chemikalien GmbH and is characterized by the following structure:

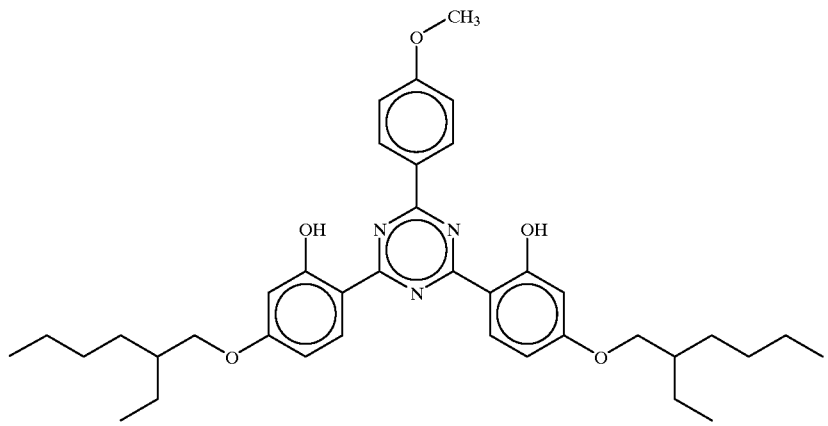

Also advantageous is 2,4-bis{[4-(3-sulfonato-2-hydroxypropyloxy)-2-hydroxy]phenyl}-6-(4-methoxypheny)-1,3,5-triazine sodium salt, which is characterized by the following structure:

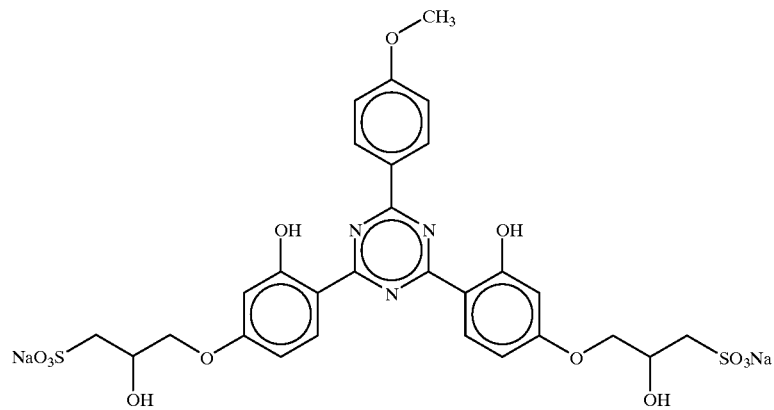

Also advantageous is 2,4-bis{[4-(3-(2-propyloxy)-2-hydroxypropyloxy)-2-hydroxy]phenyl}-6(4-methoxyphenyl)-1,3,5-triazine, which is characterized by the following structure:

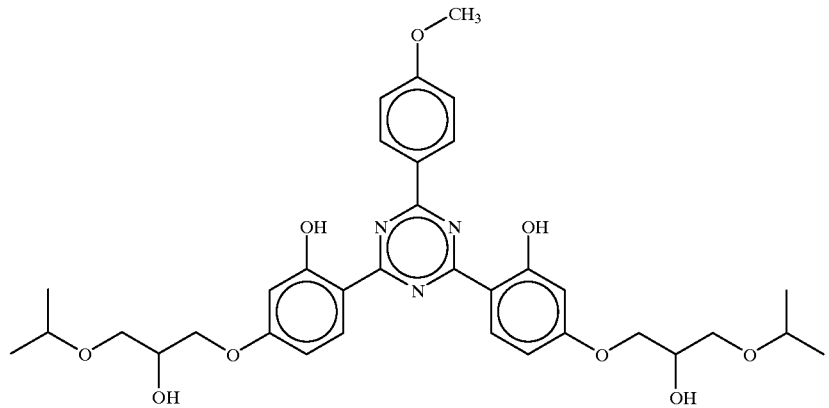

Also advantageous is 2,4-bis{[4-(2-ethylhexyloxy)-2-hydroxy]phenyl}-6-[4-(2-methoxyethoxycarbonyl)phenylamino]-1,3,5-triazine, which is characterized by the following structure:

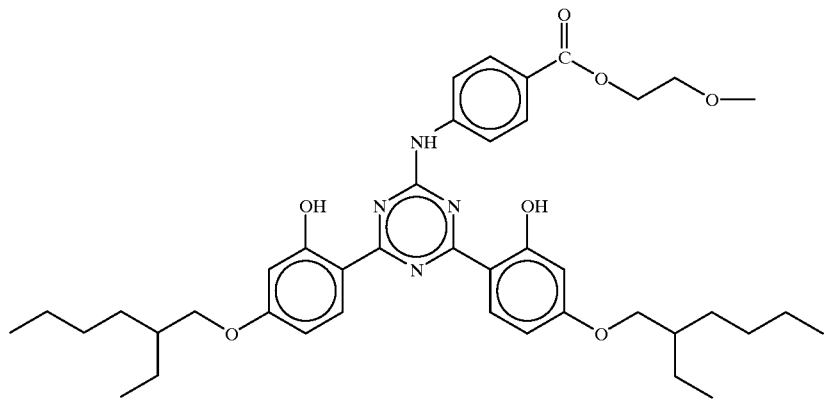

Also advantageous is 2,4-bis{[4-(3-(2-propyloxy)-2-hydroxypropyloxy)-2-hydroxy]phenyl}-6-[4-(ethoxycarbonyl)phenylamino]-1,3,5-triazine which is characterized by the following structure:

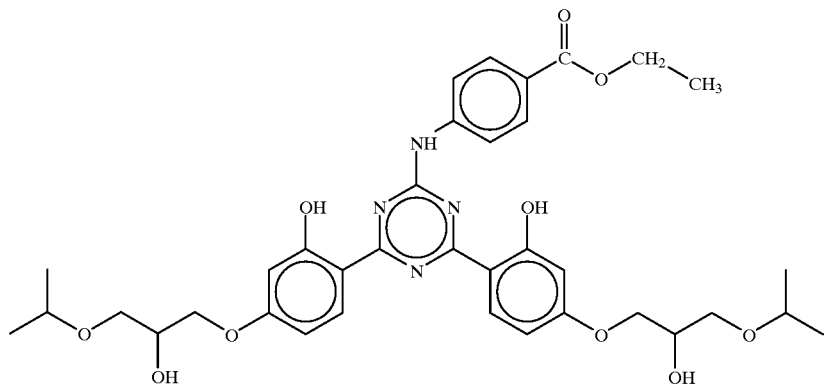

Also advantageous is 2,4-bis{[4-(2-ethylhexyloxy)-2-hydroxy]phenyl}-6-(1-methylpyrrol-2-yl)1,3,5-triazine, which is characterized by the following structure:

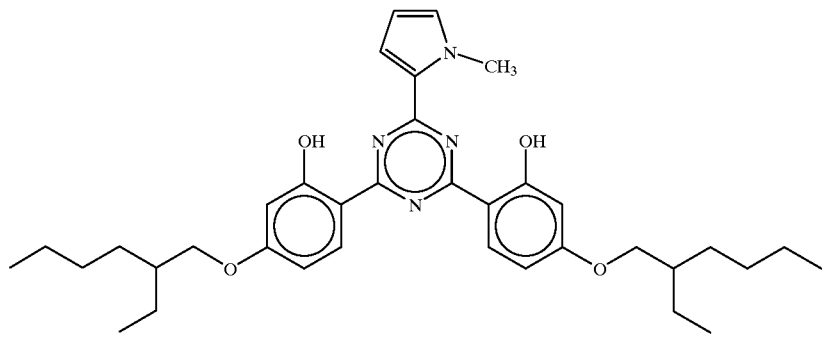

Also advantageous is 2,4-bis{[4-tris(trimethylsiloxysilylpropyloxy)-2-hydroxy]phenyl}-6-(4-methoxyphenyl)-1,3,5-triazine, which is characterized by the following structure:

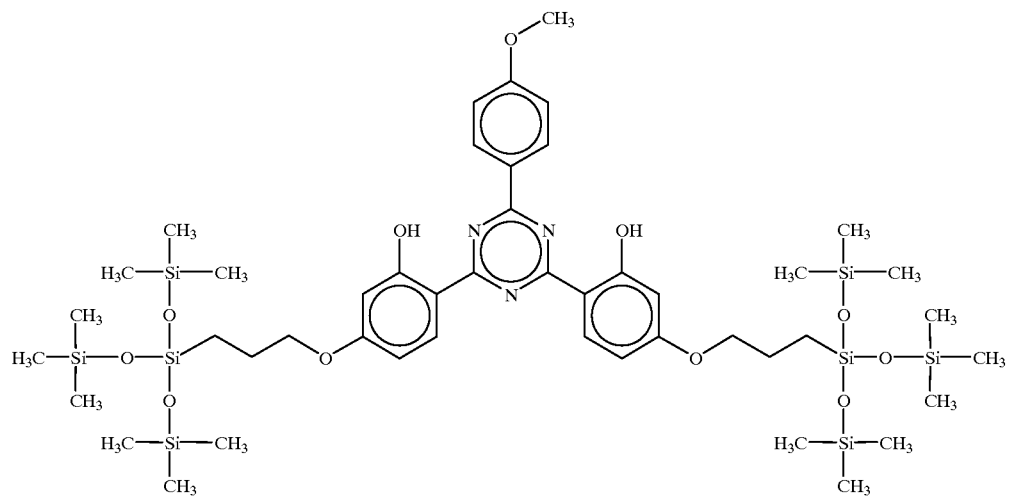

Also advantageous is 2,4-bis{[4-(2-methylpropenyloxy)-2-hydroxy]phenyl}-6-(4-methoxyphenyl)-1,3,5-triazine, which is characterized by the following structure:

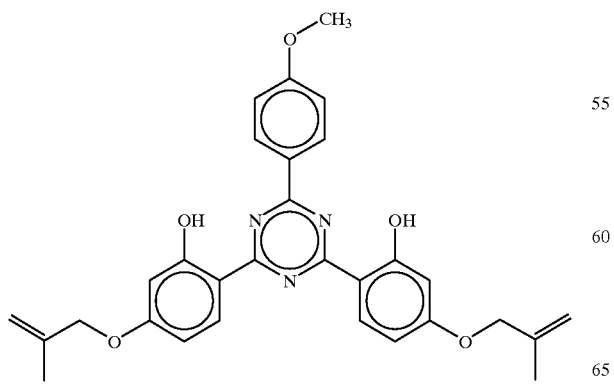

Also advantageous is 2,4-bis{[4-(1',1',1',3',5',5',5'-heptamethylsiloxy-2-methylpropyloxy)-2 hydroxy]-phenyl}-6-(4-methoxyphenyl)-1,3,5-triazine, which is characterized by the following structure:

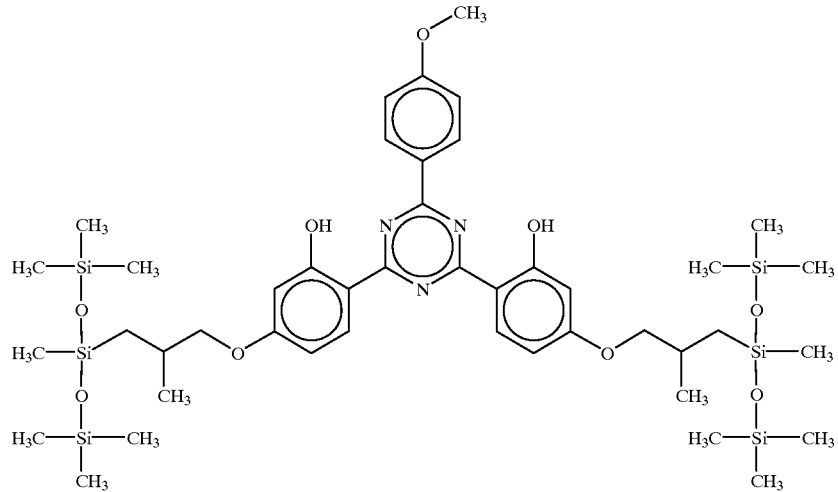

In a particularly preferred embodiment, the present invention relates to cosmetic or dermatological formulations with a content of an asymmetrically substituted s-triazine whose chemical structure is represented by the formula

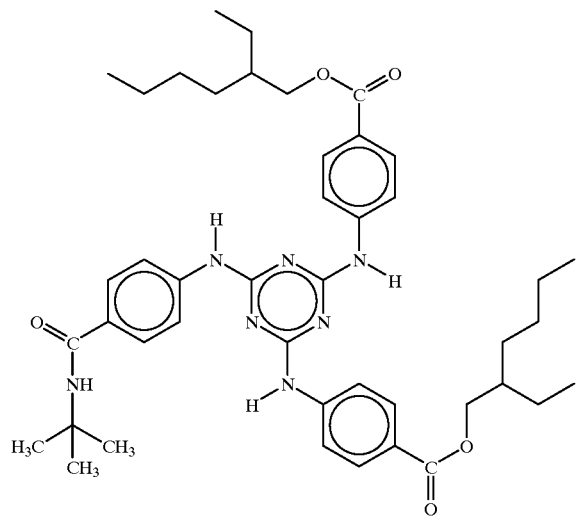

which is also referred to hereinafter as dioctylbutylamidotriazone (INCI) and is obtainable under the proprietary name UVASORB HEB from Sigma 3 V.

The asymmetrically substituted s-triazine derivative(s) of the invention are advantageously incorporated into the oil phase of the cosmetic or dermatological formulations.

The total amount of one or more asymmetrically substituted s-triazine derivatives, in particular of dioctylbutylamidotriazone, in the finished cosmetic or dermatological preparations is advantageously chosen from the range from 0.1 to 15.0% by weight, preferably 0.5 to 10.0% by weight, based on the total weight of the preparations.

The cosmetic or dermatological light protection formulations of the invention may have conventional compositions and be used for cosmetic or dermatological light protection and for the treatment, care and cleansing of skin and/or the hair and as a make-up product in decorative cosmetics.

For use, the cosmetic and dermatological preparations are applied to the skin and/or the hair in a sufficient quantity in the manner customary for cosmetics.

The cosmetic and dermatological preparations according to the invention can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favorable antioxidants which can be used are any antioxidants suitable or conventional for cosmetic and/or dermatological applications.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The oil phase of the formulations which comprise the substance combination of the invention is advantageously chosen from the group of polar oils, for example from the group of lecithins and fatty acid triglycerides, namely the glycerol triesters of saturated and/or unsaturated, branched and/or unbranched alkanecarboxylic acids with a chain length of from 18 to 24, in particular 12 to 18, C atoms. The fatty acid triglycerides can, for example, advantageously be chosen from the group of synthetic, semisynthetic and natural oils such as, for example, caprylic/capric triglyceride, cocoa glyceride, olive oil, sunflower oil, soybean oil, peanut oil, rapeseed oil, almond oil, palm oil, coconut oil, castor oil, wheatgerm oil, grapeseed oil, safflower oil, evening primrose oil, macadamia nut oil and the like.

For the purposes of the present invention, further advantageous polar oil components can also be chosen from the group of esters of saturated and/or unsaturated, branched and/or unbranched alkanecarboxylic acids with a chain length of from 3 to 30 C atoms and saturated and/or unsaturated, branched and/or unbranched alcohols with a chain length of from 3 to 30 C atoms, and from the group of esters of aromatic carboxylic acids and saturated and/or unsaturated, branched and/or unbranched alcohols with a chain length of from 3 to 30 C atoms. Such ester oils can then be advantageously chosen from the group of octyl palmitate, octyl cocoate, octyl isostearate, octyidodecyl myristate, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyidodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters such as, for example, jojoba oil.

The oil phase can advantageously also be chosen from the group of dialkyl ethers, an advantageous example being dicaprylyl ether.

It is also preferred to choose the oil component(s) from the group of isoeicosane, neopentyl glycol diheptanoate, propylene glycol dicaprylate/dicaprate, caprylic/capric/ diglyceryl succinate, butylene glycol caprylate/caprate, $C_{12-13}$-alkyl lactate, di-$C_{12-13}$-alkyl tartrate, tri-isostearin, dipentaerythrityl hexacaprylate/hexacaprate, propylene glycol monoisostearate, tricaprylin, dimethylisosorbide. It is particularly advantageous if the oil phase in the formulations of the invention has a content of $C_{12-15}$-alkyl benzoate or consists entirely of the latter.

Any mixtures of such oil and wax components can also be advantageously employed for the purpose of the present invention.

The oil phase may likewise advantageously also contain nonpolar oils, for example those selected from the group of branched and unbranched hydrocarbons and waxes, in particular mineral oil, Vaseline (petrolatum), liquid paraffin, squalane and squalene, polyolefins, hydrogenated polyisobutenes and isohexadecane. The preferred substances among polyolefins are polydecenes.

The oil phase may also advantageously have a content of cyclic or linear silicone oils or consist completely of such oils, it being preferred, however, to use besides the silicone oil or silicone oils an additional content of other oil phase components.

Cyclomethicone (octamethylcyclotetrasiloxane) is advantageously employed as silicone oil to be used according to the invention. However, other silicone oils can also advantageously be used for the purpose of the present invention, for example cetyidimethicone, hexamethylcyclotrisiloxane, polydimethylsiloxane, poly(methylphenylsiloxane).

Also advantageous according to the invention are, for example, natural waxes of animal and plant origin, such as, for example, beeswax, chinese wax, bumblebee wax and other insect waxes, and shea butter.

The aqueous phase of the preparations of the invention may advantageously comprise conventional cosmetic auxiliaries such as, for example, alcohols, in particular those of low C number, preferably ethanol and/or isopropanol, diols or polyols of low C number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes and, in particular, one or more thickeners which may advantageously be chosen from the group of silicon dioxide, aluminum silicates, polysaccharides and derivatives thereof, for example hyaluronic acid, xanthan gum, hydroxypropylmethylcellulose, particularly advantageously from the group of polyacrylates, preferably a polyacrylate from the group of so-called carbopols, for example carbopols of types 980, 981, 1382, 2984, 5984, in each case singly or in combination. Moisturizers can also preferably be used.

Substances or mixtures of substances referred to as moisturizers are those which confer on cosmetic or dermatological preparations the property of reducing the moisture loss from the stratum corneum (also called the transepidermal water loss) (TEWL)) and/or have a beneficial effect on the hydration of the stratum corneum, after application or dispersion on the surface of the skin.

Advantageous moisturizers for the purpose of the present invention are, for example, glycerol, lactic acid, pyrrolidonecarboxylic acid and urea. It is also particularly advantageous to use polymeric moisturizers from the group of polysaccharides which are soluble in water and/or swellable in water and/or gellable using water. Particularly advantageous are, for example, hyaluronic acid, chitosan and/or a fucose-rich polysaccharide which is listed in Chemical Abstracts under the registry number 178463-23-5 and is obtainable, for example, under the name Fucogel® 1000 from SOLABIA S.A.

According to their constitution, cosmetic or topical dermatological compositions can be used for the purpose of the present invention for example as skin protection cream, cleansing milk, day or night cream etc. It is possible and advantageous where appropriate to use the compositions of the invention as the basis for pharmaceutical formulations.

Cosmetic and dermatological preparations in the form of a sunscreen composition are also beneficial. These preferably comprise in addition to the active ingredient combinations of the invention additionally at least one UV-A filter substance and/or at least one UV-B filter substance. Formulations of these types may, although not necessarily, where appropriate also comprise one or more inorganic pigments as UV filter substances.

Preferred inorganic pigments are based on metal oxides and/or other metal compounds which have low solubility or are insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$), cerium (for example $Ce_2O_3$), mixed oxides of the corresponding metals, and mixtures of such oxides.

An additional content of titanium dioxide and/or zinc oxide particles with a stabilizing effect may, of course, also be advantageous but is not necessary for the purpose of the present invention.

It is also advantageous for the purpose of the present invention to design cosmetic and dermatological preparations whose main purpose is not to protect from sunlight but nevertheless comprise a content of UV-protective substances. Thus, for example, it is usual to incorporate UV-A and UV-B filter substances into day creams.

UV-protective substances as well as antioxidants and, if required, preservatives also represent effective protection of the preparations themselves against spoilage.

Preparations of the invention preferably comprise substances which absorb UV radiation in the UV-A and/or UV-B range, the total amount of the filter substances being, for example, 0.1% by weight to 30% by weight, preferably 0.5 to 20% by weight, in particular 1.0 to 15.0% by weight, based on the total weight of the preparations, in order to provide cosmetic preparations which protect the hair or the skin from the entire range of ultraviolet radiation. They may also act as sunscreen compositions for the hair or the skin.

If the emulsions of the invention comprise UV-B filter substances, these may be oil-soluble or water-soluble. Examples of oil-soluble UV-B filters advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate, triazine derivatives symmetrical in relation to the $C_3$ axis of the basic triazine, preferably 4,4',4''-(1,3,5-triazin-2,4,6-triyltriimino)trisbenzoic acid tris(2-ethylhexylester) [INCI: octyl triazone], which is marketed by BASF Aktiengesellschaft under the trade name UVINUL® T 150, benzotriazole derivatives, preferably 2,2'-methylenebis(6-(2 H-benzotriazol-2-yl)-4(1,1,3,3-tetramethylbutyl)phenol)

and UV filters bound to polymers.

Examples of advantageous water-soluble UV-B filters are:

salts of 2-phenylbenzimidazole-5-sulfonic acid such as its sodium, potassium or its triethanolammonium salt, and the sulfonic acid itself;

sulfonic acid derivatives of benzophenones, preferably 2-hydroxy-4-methoxybenzophenone-5-sulfonic acid and its salts;

sulfonic acid derivatives of 3-benzylidenecamphor such as, for example, 4-(2-oxo-3 bornylidenemethyl) benzenesulfonic acid, 2-methyl-5-(2-oxo-3-bornylidenemethyl)-benzenesulfonic acid and their salts.

The list of UV-B filters mentioned which may be used in the preparations of the invention is, of course, not intended to be limiting.

Advantageous UV filter substances for the purpose of the present invention are in addition so-called broadband filters, i.e. filter substances which absorb both UV-A and UV-B radiation.

An advantageous broadband filter for the purpose of the present invention is 2,2'-methylenebis(6-(2H-benzotriazol-2-yl)-4-(1,1,3,3-tetramethylbutyl)phenol) which is characterized by the chemical structural formula

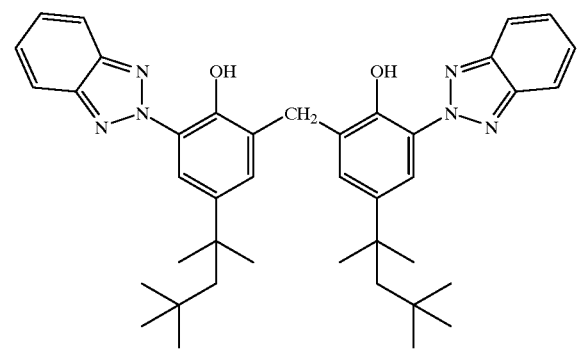

and is obtainable under the proprietary name Tinosorb®M from CIBA-Chemikalien GmbH.

An advantageous broadband filter for the purpose of the present invention is moreover 2-(2H-benzotriazol-2-yl)-4-methyl-6-[2-methyl-3-[1,3,3,3-tetramethyl-1-[(trimethylsil)oxy]disiloxanyl]propyl]phenol (CAS No.: 155633-54-8) with the INCI name drometrizole trisiloxane, which is characterized by the chemical structural formula

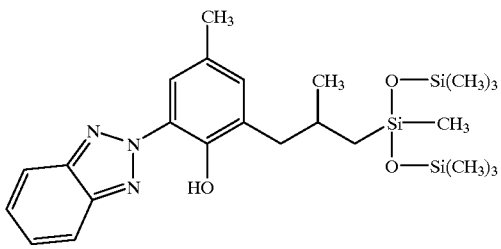

It may also be advantageous to use in preparations of the invention UV-A filters which have to date normally been present in cosmetic preparations. These substances are preferably derivatives of dibenzoylmethane, in particular 1-(4- tert-butylphenyl)-3-(4-methoxyphenyl)-propane-1,3-dione and 1-phenyl-3-(4-isopropylphenyl)propane-1,3-dione.

Further advantageous UV-A filter substances are 1,4-bis (4,6-disulfo-2 benzimidazolyl)benzene:

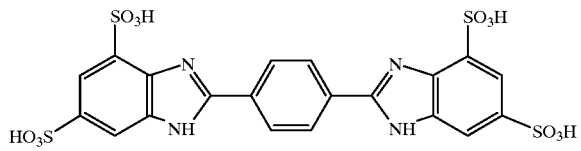

and its salts, especially the corresponding sodium, potassium or triethanolammonium salts, in particular 1,4-bis(4,6-disulfo-2-benzimidazolyl)benzene disodium salt:

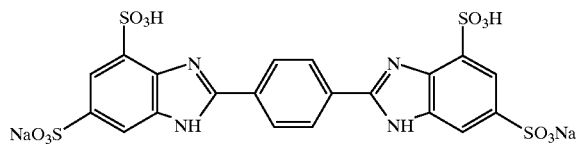

and 1,4-bis(2-oxo-10-sulfo-3-bornylidenemethyl)benzene and it salts (especially the corresponding 10-sulfonato compounds, in particular the corresponding sodium, potassium or triethanolammonium salt), which is also referred to as benzene-1,4-di(2-oxo-3 bornylidenemethyl-10-sulfonic acid) and which has the following structure:

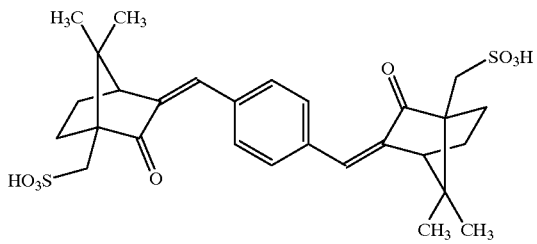

The invention also relates to preparations comprising UV-A filters. The amounts used for the UV-B combination can be employed.

It may also be advantageous where appropriate to incorporate according to the invention further UV-A and/or UV-B filters into cosmetic or dermatological preparations, for example particular salicylic acid derivatives such as 4-isopropylbenzyl salicylate, 2-ethylhexyl salicylate (=octyl salicylate), homomenthyl salicylate.

Another light protection filter substance advantageously to be used according to the invention is ethylhexyl 2-cyano-3,3-diphenylacrylate (octocrylene), which is obtainable from BASF under the name Uvinul® N 539, and which has the following structure:

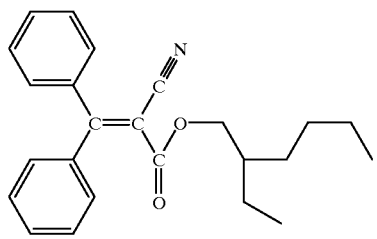

The list of UV filters mentioned, which can be employed for the purpose of the present invention, is, of course, not intended to be limiting.

The following examples are intended to illustrate the present invention without restricting it. The numerical values in the examples mean percentages by weight based on the total weight of the respective preparations.

|  | Example 1 O/W 1 | Example 2 O/W 2 | Example 3 W/O 1 | Example 4 W/O 2 | Example 5 W/O 3 |
|---|---|---|---|---|---|
| Stearic acid | 1.50 | — | — | — | — |
| Glycerol monostearate | 3.00 | — | — | — | — |
| Sorbitan stearate | — | 3.00 | — | — | — |
| Polyglyceryl-3-methyl-glucose distearate | — | 1.50 | — | — | — |
| Polyglyceryl-2 dipolyhydroxystearate | — | — | 5.00 | — | — |
| Cetyl dimethicone copolyol | — | — | — | — | 5.00 |
| PEG-30 dipolyhydroxy-stearate | — | — | — | 4.00 | — |
| Dimethicone | 2.00 | — | 2.00 | — | 5.00 |
| Phenyltrimethicone | 2.00 | — | — | 5.00 | 3.00 |
| Vitamin E acetate | 0.50 | 0.50 | — | 0.50 | — |
| Dioctylbutamidotriazone | 3.00 | — | 3.00 | — | 5.00 |
| Aniso triazine | — | 3.00 | 2.00 | 5.00 | 2.00 |
| Aerosil R972 ® | — | — | — | 0.50 | — |
| Hallbrite TQ ® | 6.00 | 8.00 | 5.00 | 4.00 | 7.00 |
| Preservative | 0.50 | 0.50 | 0.50 | 0.50 | 0.50 |
| Glycerol | 3.00 | 10.00 | 5.00 | 10.00 | 5.00 |
| MgSO₄ | — | — | 1.00 | 1.00 | — |
| NaCl | — | — | — | — | 1.00 |
| Xanthan gum | 0.30 | — | — | — | — |
| Pemulen TR1 ® | — | 0.10 | — | — | — |
| 45% Sodium hydroxide solution | 0.50 | 1.20 | — | — | 1.30 |
| Water | ad 100.00 | ad 100.00 | ad 100.00 | ad 100.00 | ad 100.00 |

|  | Example 6 ydrodispersion | Example 7 W/O Pickering emulsion | Example 8 Spray | Example 9 Spray |
|---|---|---|---|---|
| Glycerol monostearate | — | — | 4.00 | — |
| Glycerol monostearate SE | — | — | — | 4.50 |
| Ceteareth-20 | — | — | — | 1.00 |
| Ceteareth-12 | — | — | 1.50 | — |
| Dimethicone | — | — | — | 2.00 |
| Phenyltrimethicone | — | 5.00 | — | — |
| Vitamin E acetate | — | 0.50 | — | — |
| Dioctylbutamidotriazone | 2.00 | 5.00 | — | 2.00 |
| Aniso triazine | 2.00 | 5.00 | 2.00 | — |
| Eusolex T2000 ® | — | 4.00 | — | — |
| Aerosil R972 ® | — | 1.00 | — | — |
| Hallbrite TQ ® | 8.00 | 4.00 | 5.00 | 6.00 |
| Preservative | 0.50 | 0.50 | 0.50 | 0.50 |
| Glycerol | — | 3.00 | 10.00 | 5.00 |
| Xanthan gum | 0.50 | — | — | — |
| Pemulen TR1 ® | 0.30 | — | — | — |

-continued

| | | | | |
|---|---|---|---|---|
| 45% Sodium hydroxide solution | 0.30 | — | 0.40 | — |
| Water | ad 100.00 | ad 100.00 | ad 100.00 | ad 100.00 |

What is claimed is:

1. A cosmetic or dermatological composition effective for light protection which is comprised of:
   (a) one or more asymmetrically substituted triazine UV filter compounds; and
   (b) one or more dialkyl naphthalates having the structural formula

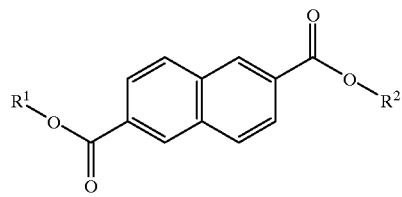

wherein $R^1$ and $R^2$ are, independently of one another, branched or unbranched alkyl groups having 6 to 24 carbon atoms.

2. The composition of claim 1, wherein the dialkyl naphthalate is diethylhexyl naphthalate.

3. The composition of claim 1, wherein the asymmetrically substituted triazine compounds are selected from the group consisting of:
   2,4-bis{[4-(2-ethylhexyloxy)-2-hydroxy]phenyl}-6-(4-methoxyphenyl)-1,3,5-triazine;
   2,4-bis{[4-(3-sulfonato-2-hydroxypropyloxy)-2-hydroxy]phenyl}-6-(4-methoxyphenyl)-1,3,5-triazine sodium salt;
   2,4-bis{[4-(3-(2-propyloxy)-2-hydroxypropyloxy)-2-hydroxy]phenyl}-6-(4-methoxyphenyl)-1,3,5-triazine;
   2,4-bis{[4-(2-ethylhexyloxy)-2-hydroxy]phenyl}-6-[(4-2-methoxyethoxycarbonyl)-phenylamino]-1,3,5-triazine;
   2,4-bis{[4-(3-(2-propyloxy)-2-hydroxypropyloxy)-2-hydroxy]phenyl}-6-[(4-ethoxycarbonyl)phenylamino]-1,3,5-triazine;
   2,4-bis{[4-(2-ethylhexyloxy)-2-hydroxy]phenyl}-6-(1-methylpyrrol-2-yl)-1,3,5-triazine;
   2,4-bis{[4-tris(trimethylsiloxysilylpropyloxy)-2-hydroxy]phenyl}-6-(4-methoxyphenyl)-1,3,5-triazine;
   2,4-bis{[4-(2-methylpropenyloxy)-2-hydroxyl]phenyl}-6-(4-methoxyphenyl)-1,3,5-triazine;
   2,4-bis{[4-(1',1',1',3',5',5',5'-heptamethylsiloxy-2-methylpropyloxy)-2-hydroxy]phenyl}-6-(4-methoxyphenyl)-1,3,5-triazine; and
   dioctylbutylamidotriazone.

4. A method of solubilizing or stabilizing an asymmetrically substituted triazine compound which comprises of adding a solubilizing or stabilizing effective amount of one or more dialkyl napthalates having the structural formula:

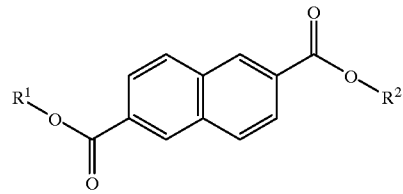

in which $R^1$ and $R^2$ are, independently of one another, branched and unbranched alkyl groups having 6 to 24 carbon atoms, to said asymmetrically substituted triazine compound.

5. A method of solubilizing or increasing the solubility of an asymmetrically substituted triazine compound in:
   (a) an isolated oil component; or
   (b) at least one oil phase of a disperse two-phase or multiphase system which optionally comprises of one or more aqueous phases,
   which comprises of adding a solubilizing or stabilizing effective amount of one or more dialkyl naphthalates having the structural formula:

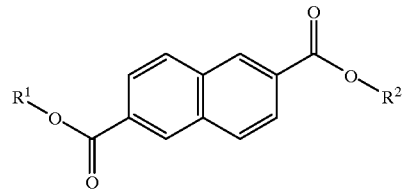

in which $R^1$ and $R^2$ are, independently of one another, branched and unbranched alkyl groups having 6 to 24 carbon atoms to said asymmetrically substituted triazine compound.

6. A method of protecting the skin from UV light which comprises of administering to a patient in need thereof an effective amount of the composition of claim 1.

* * * * *